United States Patent [19]

Burstein et al.

[11] Patent Number: 4,691,332
[45] Date of Patent: Sep. 1, 1987

[54] HIGH ENERGY COMPUTED TOMOGRAPHY

[75] Inventors: Paul Burstein, Arlington; Allen Krieger, Lexington; Martin Annis, Cambridge; Richard C. Chase, Tewksbury, all of Mass.

[73] Assignee: American Science and Engineering, Inc., Cambridge, Mass.

[21] Appl. No.: 589,443

[22] Filed: Mar. 14, 1984

Related U.S. Application Data

[63] Continuation-in-part of Ser. No. 474,937, Mar. 14, 1983, abandoned.

[51] Int. Cl.$^4$ ............................................. G01N 3/02
[52] U.S. Cl. ...................................... 378/7; 378/11; 378/17
[58] Field of Search ............... 378/7, 4, 17, 11, 147, 378/21; 250/363 S, 445

[56] References Cited

U.S. PATENT DOCUMENTS 3,766,387  10/1973  Heffan et al. ..................... 378/17
4,593,355   6/1986  Chase ................................ 378/21

OTHER PUBLICATIONS

"Computerized Tomography Inspection of Trident Rocket Motors: A Capability Demonstration", Materials Evaluation, vol. 40, No. 12, pp. 1280–1284 (1982) Burstein et al.

Primary Examiner—Salvatore Cangialosi
Attorney, Agent, or Firm—Pollock, Vande Sande & Priddy

[57] ABSTRACT

Computerized axial tomography is employed with respect to large relatively dense objects such as a solid fuel rocket engine. High energy X-rays, such as a 15 MeV source is used. To develop clean images, a collimator is employed with a relatively minute acceptance angle. Acceptance angles on the order to 1°, and in a preferred embodiment 7 minutes of a degree, are used. In a preferred embodiment, the collimator may be located between the object and the detector, although in other embodiments, a pre-collimator may also be used, that is between the X-ray source and the object being illuminated.

12 Claims, 5 Drawing Figures

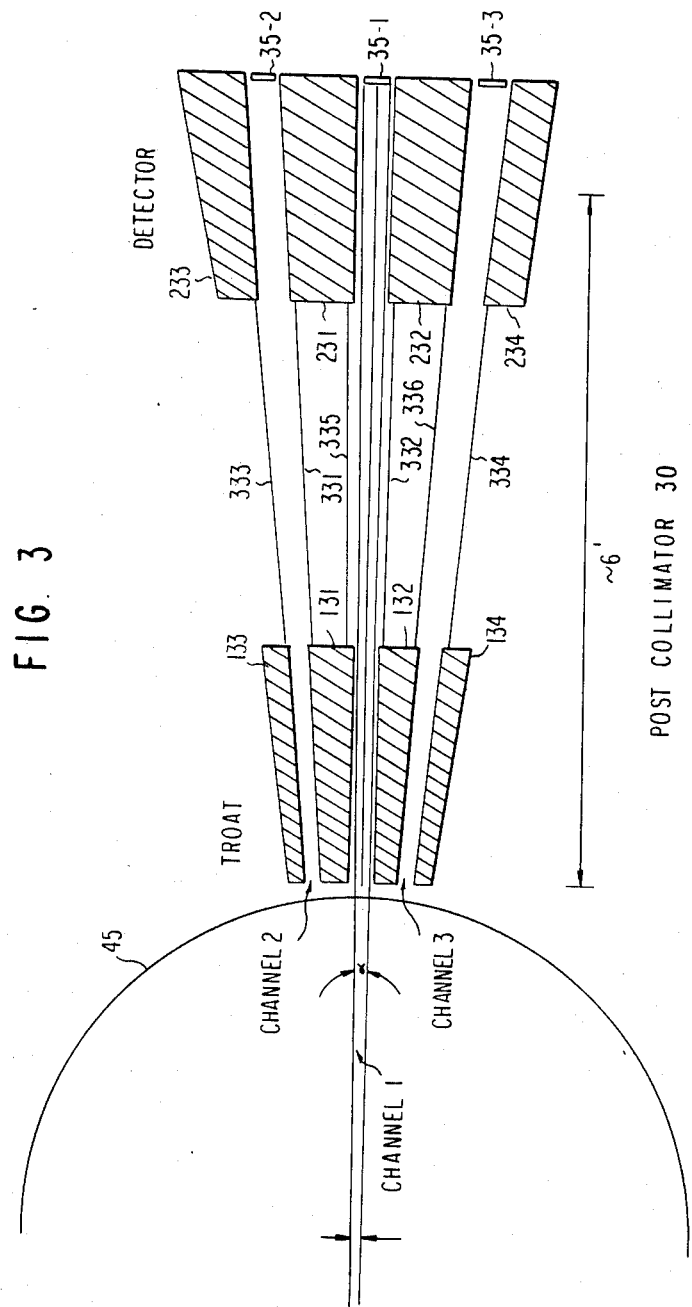

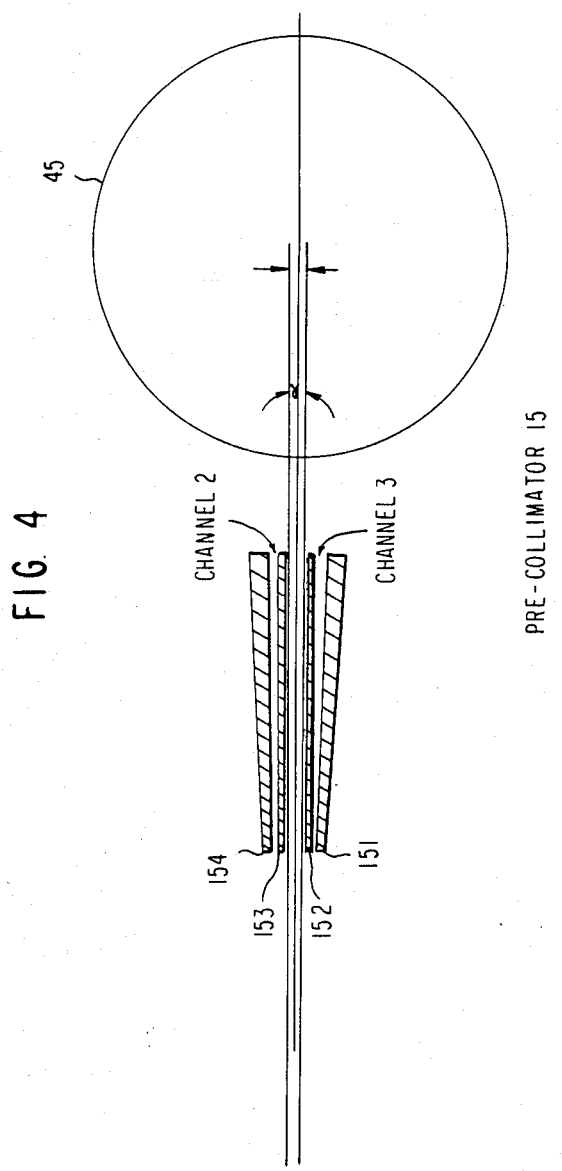

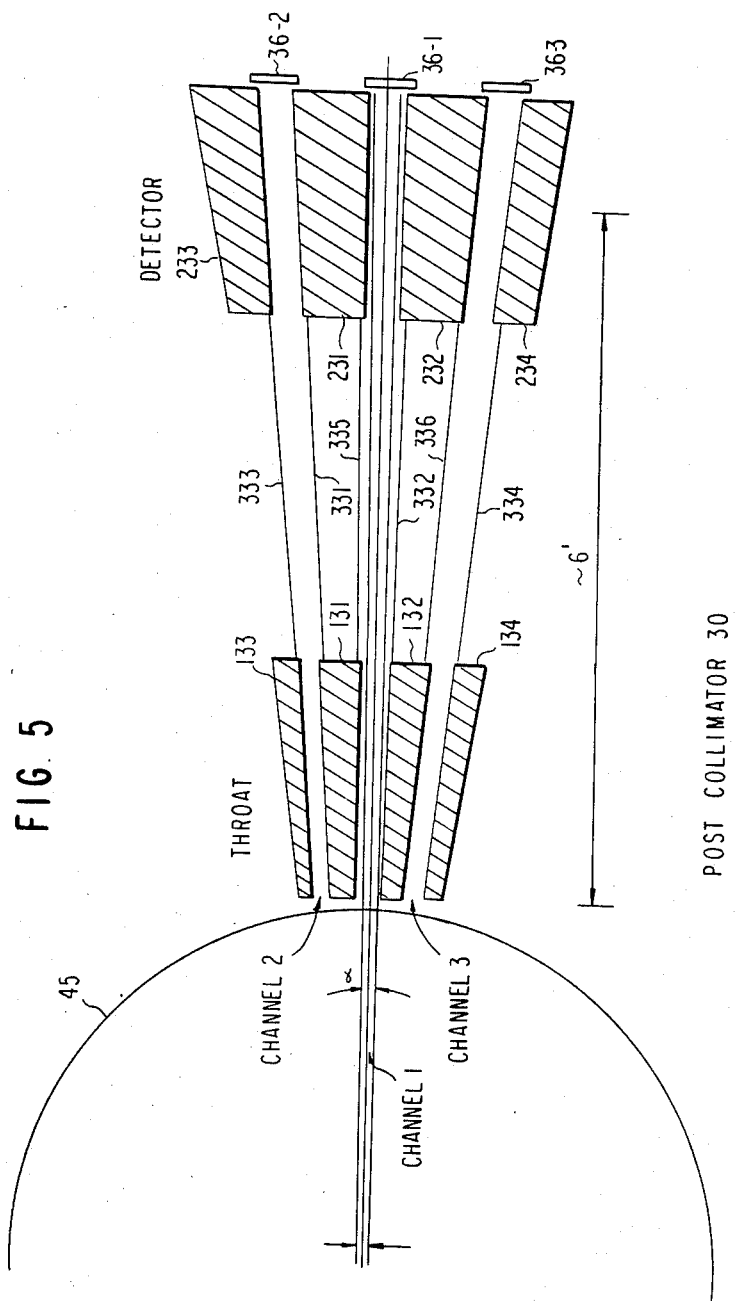

HIGH ENERGY COMPUTED TOMOGRAPHY

REFERENCE TO CO-PENDING APPLICATION

This application is a continuation-in-part of application Ser. No. 474,937, filed Mar. 14, 1983, now abandoned.

FIELD OF THE INVENTION

The present invention relates to high energy tomography, more particularly tomography employing energy sources, e.g. one million electron volts or higher.

BACKGROUND ART

Computed tomography (abbreviated CT) has opened whole new applications for the general subject of imaging employing penetrating radiant energy. Prior to computed tomography, imaging employing penetrating radiant energy was substantially limited to production of radiant energy shadow graphs (sometimes called a projection radiograph), i.e. the typical X-ray image. Such images suffered from a number of drawbacks which limited the utility of the resulting product. Because the projection radiograph provided only a shadow image, distinct objects lying in the path between the source of penetrating radiant energy and a film plane produced shadows of those objects which were superimposed one on another. This made it difficult for one interpreting such an image to distinguish one object from another, to delineate the shape of the different objects, to determine their relative densities and/or relative positions.

In computed tomography, no film is used, instead one or more radiant energy detectors are used. A source of penetrating radiant energy is directed at the location of the detector or detectors, and the object to be imaged is moved relative to the source/detector arrangement. Depending on the configuration of the source of penetrating radiant energy and the configuration of the detector and/or detectors, that motion may be limited to simple rotation, or it may be a more complicated motion consisting of translation and rotation. Regardless of these variables, a requirement for computed tomography is the production of a plurality of "views" of the object being imaged. Each view consists of absorption data describing the transmissivity of the object being imaged at a single angle relative to the source/detector arrangement. After obtaining similar absorption data for a plurality of views, the entire ensemble of absorption data is convolved and back-projected so as to produce an image corresponding to a cross section of the object being imaged taken at the plane of the object through which the penetrating radiant energy is directed. Different cross sections, or slices, are produced by repeating the foregoing steps with the illumination directed at different cross sections of the object to be imaged.

By far the most widespread application of computed tomography is in the medical field wherein images useful in diagnostic procedures are employed. As can be easily understood, the design of computed tomography equipment for medical applications is selected so as to optimize the resulting image. To this end, for example, the illuminating source is typically an X-ray source of energy in the range of 150 kilovolts.

Computed tomography, however, is not limited to the medical field and has wide applicability in the general field of non-destructive testing. There are many objects in which a cross section image would be very valuable. For purposes of describing this invention, a solid fuel rocket motor will be taken as exemplary of a wide variety of objects, a cross section of which would be very desirable. These objects all have in common a number of characteristics, for example they are:

1. much more dense than internal human organs, areal density may be measured in hundreds of grams per square centimeter,
2. they are not restricted to the same size scale as human organs, although it may be desirable to be able to view minute portions (measured on the order of thousandths of an inch or less) in an object with a diameter measured in the range of many feet.

Although imaging such objects using penetrating radiant energy has, in the past, been employed, see for example Heffan et al U.S. Pat. Nos. 3,766,387; Mauch et al 3,894,234 (related to rocket motors); Stewart 3,992,627 (related to gas turbine engines); Kenney et al 3,769,507 (related to optically opaque objects including components of the human body as well as metal castings, pipes, plates, complex mechanical devices, etc.); and Cherry 3,008,049, to the best of applicants' knowledge, computed tomography has not been employed with relatively dense and large objects such as rocket motors so as to produce images which can be used to delineate small defects such as cracks, voids and separations with dimensions measured on the scale of thousandths of an inch located anywhere within the motor.

As indicated in Kenney et al, the key to conventional radiography is differential absorption of radiation where variations in thickness, density and chemical composition provide differing attenuation for the penetrating radiant energy. Kenney indicates, however, that the absence of significant density differences, for example a hairline crack in a metal casing, etc., makes it almost impossible to successfully detect such discontinuities. Kenny also indicates that in conventional radiography, scattered radiation is considered undesirable because it results in fogging and poor definition of the radiograph. This is also true in computed tomography wherein scattering degrades the view and renders accurate back projection impossible. While Kenney indicates the effects of scattered radiation are minimized by the use of lead screens or diaphragms, the use of such screens and/or diaphragms becomes less and less attractive as the energy of the penetrating radiant energy increases, because as the energy increases a given quantity of lead has less and less of an effect. For other examples of collimation, see Wilson, Jr., U.S. Pat. No. 3,151,245; Ashe et al U.S. Pat. No. 4,096,389; and Wagner U.S. Pat. No. 4,286,156.

It is therefore one object of the present invention to provide an apparatus for computed tomography on highly opaque objects of significant size wherein it is desired to image portions of the object which may be very much smaller than the thickness of any material which can collimate the illuminating energy. It is another object of the present invention to provide an apparatus for producing computed tomography using high energy illumination (one million) electron volts or more).

SUMMARY OF THE INVENTION

The invention meets these and other objects by providing a clean view, of an object being illuminated, to a detector. Application of those techniques for collimating penetrating radiant energy measured in low six-figure electron volt energy is simply inadequate to provide the clean view necessary for computed tomography, especially with such high energy sources. Experimental work performed by the applicants has indicated that whereas low six-figure electron volt energy penetrating radiant energy is relatively isotropically scattered, the high energy radition employed in accordance with the invention has a significantly different scattering signature. Such high energy penetrating radiant energy (one million electron volts or more) is typified by very highly forward peaked scattering. This scattering profile puts a significantly higher burden on collimating optics than the lower energy radiation employed in medical computed tomography, for example.

Taking the case of imaging a solid fuel rocket motor as exemplary, the source chosen for illumination is a Varian Linatron L-6000. This is a 15 MeV source rated at 6000 Rad/minute, measured one meter from the source. Whereas the low six-figure electron volt source (typical of the medical field) exhibits a mean scatter angle of about 60°, the high energy source such as described above exhibits a mean scatter angle of about 4°. Other experimental work indicates that the direct beam attenuation offered by lead to a source of this energy is exponentially decreasing as a function of thickness of lead between source and detector. The exponent is of the form of X/XO, where X is the actual thickness of lead and XO is about 0.85 inch. In order to obtain a good clean view of an object with large transmission variations, scattering must be below the signal strength by a factor of at least 1000 to 1, and preferably 10,000 to 1. Our experimental work indicates that this scattering reduction requires at least eight inches of lead at 15 MeV.

The combination of the high energy source, and the very dense rocket motor exacerbates the scattering problem. We believe that a collimator is essential to adequate reduction of the scattering component, and the collimation must provide an acceptance angle to an associated detector which is substantially less than 1°. In an embodiment of the invention which has actually been constructed and tested, the acceptance angle of the collimator was on the order of 7 minutes of a degree.

In one specific embodiment of the invention, the alignment procedure is simplified by providing an arrangement in which the collimator not only defines the acceptance angle of the detector, but actually defines the field of view of the detector as well. This is implemented by providing a detector whose dimensions exceed the aperture of the collimator.

Accordingly, in one aspect the invention provides a system for high energy CT imaging of targets of substantial size and density comprising:

a source of high energy penetrating radiant energy, a plurality of radiant energy detectors spaced from said source, means for supporting a target of substantial size and density between said source and said detectors for relative movement in a direction transverse to an axis connecting said source and detectors and for relative rotation about a second axis perpendicular to a plane including said source and said detectors, wherein the improvement comprises:

collimating means for restricting an acceptance angle of said detectors to substantially less than 1°.

In accordance with another aspect, the invention provides a method of high energy CT imaging comprising:

illuminating a target of substantial size and density with photons of energy in excess of one million electron volts, detecting photons transmitted by said target at one or more detectors, and translating and rotating said target relative to said source/detectors to provide plural views of said target, wherein the improvement comprises:

inhibiting detection of scattered photons by limiting an acceptance angle of said detection step to substantially less than 1°.

Depending upon the required characteristics of a final image, the collimation may be provided by a single collimator located between the target and the detector or detectors. On the other hand, the signal can be still further improved by providing a further collimator located between the source and the target. In the case of use of both collimators, the designation pre-collimator and post-collimator are used. Accordingly, if desired the method and/or apparatus of the invention can be enhanced by the addition of a pre-collimator, or a step of pre-collimating the illumination energy.

BRIEF DESCRIPTION OF THE DRAWINGS

The present invention will now be described in further detail so as to enable those skilled in the art to make and use the same in connection with the following portions of this description when taken in conjunction with the attached drawings in which:

FIG. 3 is a cross section of the post-collimator 13 in relation to the detectors and object 45;

FIG. 4 is a cross section of the pre-collimator 15 in relation to the object 45; and FIG. 5 is a cross section of a different embodiment of the invention which shows the post-collimator 13 in relation to the detectors and the object 45, and in which the field of view of the detectors is defined by the geometry of the post-collimator 13.

DETAILED DESCRIPTION OF PREFERRED EMBODIMENTS

Figure 1:
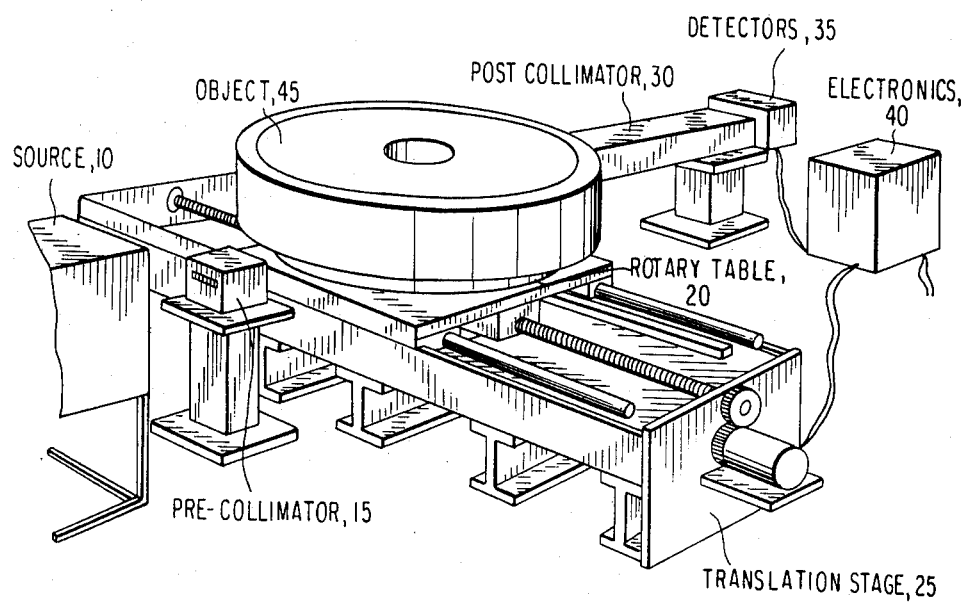
FIG. 1 is an isometric view of the components of the invention.

FIG. 1 is an illustration of the inventive system for high intensity CT imaging. More particularly, schematically illustrated as source 10 is the high energy, multiple MeV source 10. An object to be imaged 45 is located on a rotary table 20 which itself is located on a translation stage 25. FIG. 1 illustrates an embodiment of the invention actually used for testing the invention on a sample slice of a rocket motor. In actually practicing the invention on an entire rocket, weighing on the order of 60 tons, the source/detector is translated while the rocket is rotated. Different vertical slice positions are provided by an elevator set under the rocket. A detailed illustration of the apparatus to provide the required relative motion in this case (wherein the source/detector is subject to translation) can be found in the copending Mastronardi application Ser. No. 388,879, filed June 16, 1982, the disclosure of which is incorporated herein by reference. As is well known to those skilled in the CT field, the combination of rotary table 20 and translation stage 25 provides the motion of the object 45 with respect to the source/detector arrangement necessary to supply the absorption data at a plurality of different views. On the other hand, and as is disclosed in the copending application, other apparatus can provide for relative movement of the object in a direction transverse to an axis connecting the source and detectors, and for rotation about a second axis perpendicular to a plane including the source and detectors.

The radiation emitted by the source 10 is shaped by a pre-collimator 15. The collimator 15 includes a number of slits (corresponding in number to the number of detectors) for shaping the emitted radiation. In accordance with the high energy of the source 10, the pre-collimator 15 has a substantial dimension along the axis linking the source and detectors, which is necessary for appropriate attenuation of energy travelling in non-preferred directions. As has been mentioned above, the use of a pre-collimator 15 is not essential to the invention, and thus the pre-collimator 15 may be omitted.

The radiant energy emitted by the object 45 passes through a post-collimator 30 before impinging on the detectors 35. In the example being described, there are a plurality of individual detectors in the bank of detectors 35. The signal from the detectors 35 is coupled to the electronics 40 for storage and processing in a manner well known to those skilled in the art.

The post-collimator 30 provides for an effective limit on the acceptance angle of the detectors 35. Limiting the acceptance angle on the detectors 35 limits the extent to which scatter degrades the resulting image.

Figure 2:
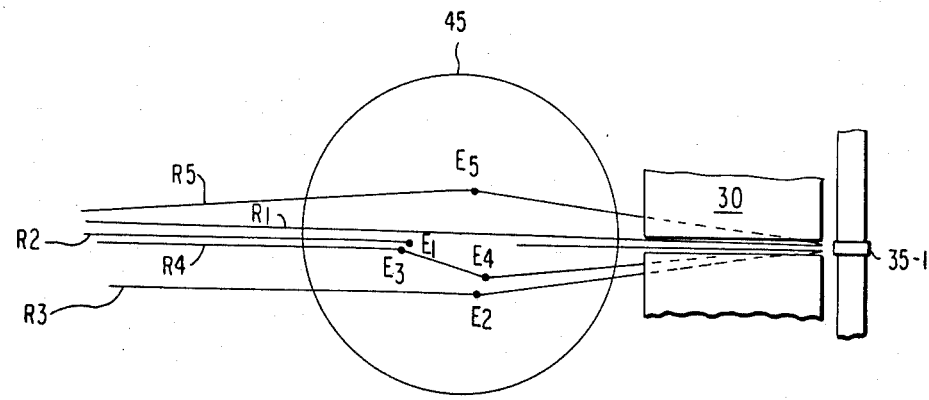
FIG. 2 is a schematic illustration showing the events giving rise to scattering which should be eliminated.

FIG. 2 illustrates a cross section of the object 45, in the plane of the imaging radiation, along with the cross sections of the collimator 30 and detector 35-1, all in the plane of the imaging radiation. For purposes of this description, we will consider four different rays, R1-R4. As is illustrated in FIG. 1, R1 travels an unimpeded path from the source, through the object, through the collimator 30 and is detected at the detector 35-1. On the other hand, R2 proceeds from the source 10, but interacts at E1. For purposes of this description, we consider that the interaction occurring at E1 results in absorption of a photon. As a result, R2 is not counted by the detector 35-1. This illustrates the manner in which absorption data is detected for later back-projection. Of course, for accurate back-projection it is essential that the data accumulated by detector 35-1 correspond to the single path or channel existing between the source 10 and the detector 35-1. Consider, for example, R3. R3 is clearly outside of this channel and therefore data corresponding to R3 should not be detected, for detection of such data will corrupt the resulting image. As is shown in FIG. 2, R3 proceeds from the source 10, enters the object 45, and interacts at location E2. This interaction produces a scattered photon, the angle of its path is now altered so that absent the collimator 30 R3 would also be detected by the detector 35-1. A similar, although less probable occurrence is illustrated with respect to R4. R4 proceeds from the source 10, enters the object 45 and interacts at E3, producing a scattered photon, whose direction has been changed. Absent further interaction, the photon proceeding from E3 would not be detected at detector 35-1 because of its direction. However, this photon further interacts at E4 again changing its direction so that it would be detected by detector 35-1 and thus result in further corruption of the image. The corruption of the image by R3 and R4 is prevented by the post-collimator 30. There are other, similar doubly interacting rays which will not be detected because of post-collimator 30. A similar problem is presented by ray R5. This ray enters the object 45 at an angle that would ordinarily prevent its detection. However, it interacts at $E_5$ and as a result it changes direction. The fact that the interaction occurs at $E_5$, outside of the channel viewed by the detector, indicates that if detected, R5 will also corrupt the image. Detection of R5 is prevented by post-collimator 30. Note, however, that this ray, and others similar to it (not parallel to R1-R2) are also prevented by a pre-collimator 15. In fact, many of the corrupting rays can be prevented by a pre-collimator 15.

Because of the statistical nature of the resulting image, 100% blockage of scattering is not essential, i.e. blocking enough to reduce the S/N ratio of $10^3$ or $10^4$ is adequate.

Although scattering and the resulting image corruption is present in all CT imaging, the problem in imaging solid fuel rocket motors is more acute for two reasons. In the first place, the size and density of the object dictates that a high energy source, in excess of one million electron volts, is required for reasonable scanning times. With lower energy sources (for example, with 150 KeV sources), the mean scattering angle is about 60° and thus much of the scattered energy is scattered at an angle so great that it will not be detected. On the other hand, with the 15 MeV source employed herein, the mean scattering angle is about 4°. Thus, a much larger percentage of the scattered energy will be scattered through so small an angle that absent other measures, it would be detected and result in image degradation. Further complicating the problem is the energy level itself requiring massive shielding for effective collimation. As will be described below, one element of the collimator 30 is a lead shield eight inches thick. This is required to cut down the scattered energy by a factor $10^4$.

FIG. 3 is a schematic of the post-collimator 30, and its relation to the object being imaged 45. FIG. 3 is a cross section taken in the plane of the illuminating radiation. The post-collimator 30 includes elements of relatively massive lead shielding in both the throat and detector regions, each of these elements of lead shielding have a length, in the direction of the illuminating radiation, on the order of eight inches. In each region, pairs of the elements form channels, three channels being shown in FIG. 3, although those skilled in the art will be aware that the number of channels can be varied to suit the desired number of detectors; in an actual embodiment of the invention that has been constructed, five detectors and thus five channels were employed. Taking up channel one (including the detector 35-1) as illustrative, the channel consists of a pair of massive lead shields in the throat region 131 and 132, a pair of equally massive interdetector shields in the detector region 231 and 232, and a pair of relatively thin lead plates 335 and 332. Although the facing edges of elements 131–132, 335–332 and 231–232 appear to be parallel in FIG. 3, actually they are converging. The channel is dimensioned so as to limit the field of view of the detector (35-1, for example). In the embodiment that has been constructed, the field of view of the detector, at the center of the object being imaged 45 was two millimeters. The channels associated with detectors 35-2 and 35-3 are arranged to view similar two millimeter fields, adjacent to the two millimeter field imaged by channel 1. Preferably, the aperture angle of the channel, that is the angular spread of radiation that will be accepted, and detected by the detector 35-1 is substantially less than 1°. In the embodiment that has been constructed, this angle was on the order of 10 minutes of a degree. The same acceptance angle applies to each other channel.

FIG. 4 is a cross section of a pre-collimator 15, corresponding to the post-collimator 30 shown in FIG. 3. More particularly, it will be seen that the pre-collimator 15 consists of a plurality of elements of relatively massive lead shielding, for example in the embodiment that has been constructed the length of each of the elements of lead shielding extending in the direction of the illuminating radiation is on the order of eight inches. Pairs of the elements form different illumination channels 1–3. Opposing faces of elements 152 and 153 form channel 1, the opposing faces of elements 153 and 154 form channel 2, and the opposing faces of elements 151 and 152 form channel 3. Although these opposing faces appear parallel in FIG. 4, in actuality they are converging so that each provides for illuminating adjacent fields of view at the center of the object 45 being illuminated. In one example, those adjacent fields of view are each on the order of 2 millimeters, and of course the angle shown in FIG. 4 is identical to the angle shown in FIG. 3.

FIG. 5 is a schematic of the post-collimator 30, and its relation to the object being imaged 45, in a manner entirely similar to FIG. 3. Moreover, those components which are identical to FIG. 3 carry the same reference characters. The only difference between FIGS. 3 and 5 is that in FIG. 3 the exemplary detectors 35-1 through 35-3 are shown as smaller in dimension that the distance between the elements 231–232 defining channel 1, 231–233 defining channel 2, and 232–234 defining channel 3. On the other hand, as shown in FIG. 5 the corresponding detectors 36-1 through 36-3 are larger in dimension than the exit apertures of the various channels. Consequently, at least for the embodiment shown in FIG. 5, the field of view of each of the detectors is defined not by the geometry of the detectors, but rather by the geometry of the post-collimator 30. Those skilled in the art will understand that this significantly aids in aligning the apparatus.

We claim:

1. A system for a high energy CT imaging of targets of substantial size and density comprising:
 a source of penetrating radiant energy of energy in excess of one million electron volts,
 a plurality of radiant energy detectors spaced from said source,
 means for supporting a target of size and density substantially greater than a human body between said source and said detectors for relative movement in a direction transverse to an axis connecting said source and said detectors and for relative rotation about a second axis perpendicular to a plane including said source and said detectors, wherein the improvement comprises:
 collimating means for restricting an acceptance angle of said detectors to substantially less than 1 degree.

2. A system of claim 1 wherein said acceptance angle is on the order of 10 minutes.

3. The system of claim 1 wherein said acceptance angle is on the order of 10 minutes and said collimating means includes a first collimator located between said source and said target, and a second collimator located between said target and said detectors.

4. The apparatus of claim 3 wherein said source provides radiation at energies substantially greater than one million electron volts.

5. The method of claim 1 wherein said target has an areal density on the order of hundreds of grams per square centimeter and a diameter on the order of several feet.

6. A method of high energy CT imaging comprising:
 illuminating a target of size and density greater than a human body with illuminating photons of energy substantially in excess of 1 million electron volts,
 detecting photons transmitted by said target at one or more detectors, and
 translating and rotating said target relative to said source/detectors to provide plural views of said target, wherein the improvement comprises:
 inhibiting detection of scattered photons by limiting an acceptance angle of said detection step to substantially less than 1 degree.

7. The method of claim 6 wherein said acceptance angle is on the order of 10 minutes.

8. The method of claim 6 wherein said inhibiting step comprises collimating photons transmitted by said target.

9. The method of claim 8 wherein said illuminating step includes a step of collimating illuminating photons prior to impinging on said target, and said collimation step comprises collimating photons emitted by said target.

10. The method of claim 6 wherein said target has an areal density on the order of hundreds of grams per square centimeter and a diameter on the order of several feet.

11. The apparatus of claim 1 in which at least one of said radiant energy detectors is selected to have a size, selected in connection with said collimating means so that a field of view of said selected detector is defined solely by said collimating means.

12. The apparatus of claim 2 in which at least one of said radiant energy detectors is selected to have a size, selected in connection with said collimating means so that a field of view of said selected detector is defined solely by said collimating means.

* * * * *